US008942805B2

(12) United States Patent
Shuros et al.

(10) Patent No.: US 8,942,805 B2
(45) Date of Patent: Jan. 27, 2015

(54) METHOD AND APPARATUS FOR RIGHT VENTRICULAR RESYNCHRONIZATION

(71) Applicant: Cardiac Pacemakers, Inc., St. Paul, MN (US)

(72) Inventors: Allan C. Shuros, St. Paul, MN (US); Jiang Ding, Shoreview, MN (US); Barun Maskara, Blaine, MN (US); Yinghong Yu, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/104,281

(22) Filed: Dec. 12, 2013

(65) Prior Publication Data

US 2014/0172035 A1 Jun. 19, 2014

Related U.S. Application Data

(60) Provisional application No. 61/739,198, filed on Dec. 19, 2012.

(51) Int. Cl.
*A61N 1/00* (2006.01)
*A61N 1/365* (2006.01)
*A61N 1/05* (2006.01)
*A61N 1/368* (2006.01)

(52) U.S. Cl.
CPC ............ *A61N 1/36585* (2013.01); *A61N 1/056* (2013.01); *A61N 1/365* (2013.01); *A61N 1/36514* (2013.01); *A61N 1/3682* (2013.01); *A61N 1/3684* (2013.01)
USPC .......................................................... 607/18

(58) Field of Classification Search
USPC .......................................................... 607/18
See application file for complete search history.

(56) References Cited

U.S. PATENT DOCUMENTS

| 5,810,014 | A | 9/1998 | Davis et al. |
| 5,921,937 | A | 7/1999 | Davis et al. |

(Continued)

FOREIGN PATENT DOCUMENTS

| EP | 1234597 A2 | 8/2002 |
| WO | WO-2014099595 A2 | 6/2014 |
| WO | WO-2014099595 A3 | 6/2014 |

OTHER PUBLICATIONS

"International Application Serial No. PCT/US2013/074618, International Search Report mailed Jun. 26, 2014", 6 pgs.

(Continued)

*Primary Examiner* — Robert N Wieland
(74) *Attorney, Agent, or Firm* — Schwegman Lundberg & Woessner, P.A.

(57) ABSTRACT

An apparatus comprises a cardiac signal sensing circuit and a first implantable electrode pair. At least one electrode of the first implantable electrode pair is configured for placement at a location in a right branch of a His bundle of the subject. The apparatus can include a therapy circuit and a control circuit. The control circuit can include an AH delay calculation circuit configured to calculate an optimal paced AH delay interval. The pacing stimulation location is distal to a location of RV conduction block in a right branch of the His bundle. The control circuit initiates delivery of an electrical stimulation pulse to the stimulation location in the His bundle according to the calculated paced AH delay interval and in response to an intrinsic depolarization event sensed in an atrium of the subject.

20 Claims, 6 Drawing Sheets

(56) References Cited

U.S. PATENT DOCUMENTS

| | | | |
|---|---|---|---|
| 7,096,064 B2 | 8/2006 | Deno et al. | |
| 7,269,457 B2 | 9/2007 | Shafer et al. | |
| 7,289,850 B2 | 10/2007 | Burnes | |
| 7,292,168 B2 | 11/2007 | Wesselink et al. | |
| 7,711,421 B2 | 5/2010 | Shafer et al. | |
| 7,769,451 B2 | 8/2010 | Yang et al. | |
| 7,904,158 B2 | 3/2011 | Stegemann et al. | |
| 7,912,544 B1 | 3/2011 | Min et al. | |
| 8,005,544 B2 | 8/2011 | Zhu et al. | |
| 8,010,191 B2 | 8/2011 | Zhu et al. | |
| 8,010,192 B2 | 8/2011 | Zhu et al. | |
| 8,014,861 B2 | 9/2011 | Zhu et al. | |
| 8,041,424 B2 | 10/2011 | Corbucci | |
| 8,050,756 B2 | 11/2011 | Zhu et al. | |
| 8,145,306 B2 | 3/2012 | Lessmeier et al. | |
| 8,406,899 B2 * | 3/2013 | Reddy et al. | 607/122 |
| 2002/0193836 A1 | 12/2002 | Schmidt | |
| 2011/0264158 A1 | 10/2011 | Dong et al. | |
| 2012/0053651 A1 | 3/2012 | Zhu et al. | |
| 2012/0101539 A1 | 4/2012 | Zhu et al. | |
| 2012/0101542 A1 | 4/2012 | Arcot-Krishnamurthy et al. | |
| 2012/0165893 A1 | 6/2012 | Ding et al. | |
| 2012/0239106 A1 | 9/2012 | Maskara et al. | |

OTHER PUBLICATIONS

"International Application Serial No. PCT/US2013/074618, Invitation to Pay Additional Fees and Partial Search Report mailed Apr. 9, 2014", 5 pgs.

"International Application Serial No. PCT/US2013/074618, Written Opinion mailed Jun. 26, 2014", 6 pgs.

* cited by examiner

METHOD AND APPARATUS FOR RIGHT VENTRICULAR RESYNCHRONIZATION

CLAIM OF PRIORITY

This application claims the benefit of U.S. Provisional Patent Application Ser. No. 61/739,198, filed on Dec. 19, 2012, the benefit of priority of which is claimed hereby, and which is incorporated by reference herein in its entirety.

TECHNICAL FIELD

This document relates generally to a cardiac rhythm management system and particularly, but not by way of limitation, to methods, systems and devices for right ventricular resynchronization.

BACKGROUND

The heart is the center of a person's circulatory system and includes an intrinsic electro-mechanical system for performing two major pumping functions. The left portions of the heart, including a left atrium (LA) and a left ventricle (LV), draw oxygenated blood from the lungs and pump it to body organs to provide the organs with their metabolic need for oxygen. The right portions of the heart, including a right atrium (RA) and a right ventricle (RV), draw deoxygenated blood from the body organs and pump it to lungs where the blood gets oxygenated. These pumping functions result from contractions of the myocardium of the heart. In a normal heart, a sinoatrial (SA) node, the heart's natural pacemaker, generates intrinsic electrical pulses that propagate through an electrical conduction system to various regions of the heart to excite the myocardial tissues of the cardiac muscles. For example, intrinsic electrical pulses originating from the SA node propagate through an atrio-ventricular (AV) node that is between the RA and RV. From the AV node, a specialized intrinsic conduction system is used by the electrical impulses to reach ventricular myocardial tissues, resulting in contraction activities of ventricles. This specialized conduction system includes the His bundle, the right and left conduction bundle branches that extend along the septum between the RV and LV, and the purkinje fibers that contact the ventricular myocardial tissues.

Coordinated delays of the propagations of the intrinsic electrical pulses in a normal electrical conduction system cause the various portions of the heart to contract in synchrony which results in efficient pumping functions. Heart disease can alter the normal intrinsic conduction paths. A blocked or otherwise abnormal electrical conduction can cause the heart to contract dyssynchronously, resulting in poor hemodynamic performance that may diminish the amount of blood supplied to the heart and the rest of the body. For example, a block in conduction of the electrical pulses in either of the left bundle branch or the right bundle branch can cause dyssynchrony among the ventricles (RV and LV) of the heart. Blockage of the normal conduction paths can cause intrinsic electrical pulses to conduct along alternate pathways, which can cause one ventricle to contract later with respect to the other ventricle. In such events of cardiac malfunctioning, cardiac resynchronization therapy (CRT) can be provided to resynchronize contractions of the ventricles of the heart.

An implantable medical device providing CRT to a patient having right bundle branch block (RBBB) is discussed in U.S. Pat. No. 8,041,424 entitled CARDIAC RESYNCHRONIZATION THERAPY FOR PATIENTS WITH RIGHT BUNDLE BRANCH BLOCK. A pacing system configured to compute optimal cardiac resynchronization pacing parameters using intrinsic conduction intervals is discussed in U.S. Patent Publication No. 2012/0165893, now issued as U.S. Pat. No. 8,483,827, entitled METHOD AND SYSTEM FOR DELIVERING CARDIAC RESYNCHRONIZATION THERAPY WITH VARIABLE ATRIO-VENTRICULAR DELAY.

Overview

Methods, systems and devices to correct conduction disease in the right ventricle (RV) of a subject are disclosed. A method example includes calculating, by a medical device, an optimal time interval from a sensed intrinsic atrial event to delivery of an electrical stimulation pulse to a stimulation location in a His bundle of a subject (this can be referred to as paced atrial-His bundle delay, or paced AH delay interval). The stimulation location is distal to a location of RV conduction block in a right branch of the His bundle. The method can include sensing an intrinsic depolarization event in an atrium of the subject. The method can include delivering an electrical stimulation pulse to the stimulation location in the His bundle according to the calculated paced AH delay interval, wherein the paced AH delay interval is shorter than an intrinsic AH delay interval. The intrinsic AH delay interval can include a time interval from the sensed intrinsic atrial depolarization event to a corresponding intrinsic depolarization event of the His bundle.

An apparatus example includes a first cardiac signal sensing circuit configured to sense an intrinsic depolarization event in an atrium of a subject, and a first implantable electrode pair. At least one electrode of the first implantable electrode pair is configured for placement at a location in a right branch of a His bundle of the subject. The apparatus can include a therapy circuit electrically connectable to the first implantable electrode pair and a control circuit communicatively coupled to the first cardiac signal sensing circuit and the therapy circuit. The control circuit can include an AH delay calculation circuit configured to calculate an optimal paced AH delay interval. The pacing stimulation location is distal to a location of RV conduction block in a right branch of the His bundle. The control circuit is configured to initiate delivery of an electrical stimulation pulse to the stimulation location in the His bundle according to the calculated paced AH delay interval and in response to an intrinsic depolarization event sensed in an atrium of the subject. The paced AH delay interval is shorter than an intrinsic AH delay interval.

This overview is intended to provide an overview of the subject matter of the present patent application. It is not intended to provide an exclusive or exhaustive explanation of the present subject matter. The detailed description is included to provide further information about the subject matter of the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of an example, but not by way of limitation, various embodiments discussed in the present document.

DETAILED DESCRIPTION

Conventional biventricular (BiV) pacing therapy provides pacing pulses to both ventricles such as to provide relief to a subject suffering from blockage of normal conduction pathways to one or both ventricles. Although the BiV pacing therapy is considered as an effective therapy for correcting a block of left bundle branch (often referred to as left bundle branch block or LBBB), various studies suggest that BiV pacing therapy fails to correct the dyssynchrony of the heart caused by right bundle branch block or RBBB. BiV pacing may cause electrical therapy impulses to propagate using a relatively slower cell-to-cell propagation path of the myocardial tissue of the LV rather than using the intrinsic specialized conduction system. Therefore, there is a need for providing effective device-based therapy to reduce or eliminate dyssynchrony of the ventricles caused by RBBB.

Ventricular dyssynchrony due to conduction branch block sometimes includes a prolonged or wide QRS complex due to delayed activation of a lateral ventricle wall. Because conduction fibers are organized longitudinally, a wide QRS complex may indicate that the conduction block is located proximally in the conduction branch in the His bundle. An arrhythmia pattern of chronic RBBB can result from three levels of conduction delay in the RV. The conduction delay can occur proximally in the His bundle, distal from the His bundle, or the conduction delay can be terminal and located where conduction paths transition from purkinje fibers to the myocardium. Proximal refers to a location towards the point of origin such as towards the AV node and distal refers to a location away from the point of origin, such as a location towards the ventricular apex for example. Proximal RBBB is most common site of conduction delay for the RV. Pacing the HIS bundle to treat RBBB can correct RBBB while maintaining the normal LV conduction paths. This can reduce dyssynchrony of the LV because physiologic activation of the ventricles is accomplished using the specialized intrinsic impulse conduction system and minimizes the slower cell-to-cell propagation of the electrical impulse through the myocardium.

Figure 1:
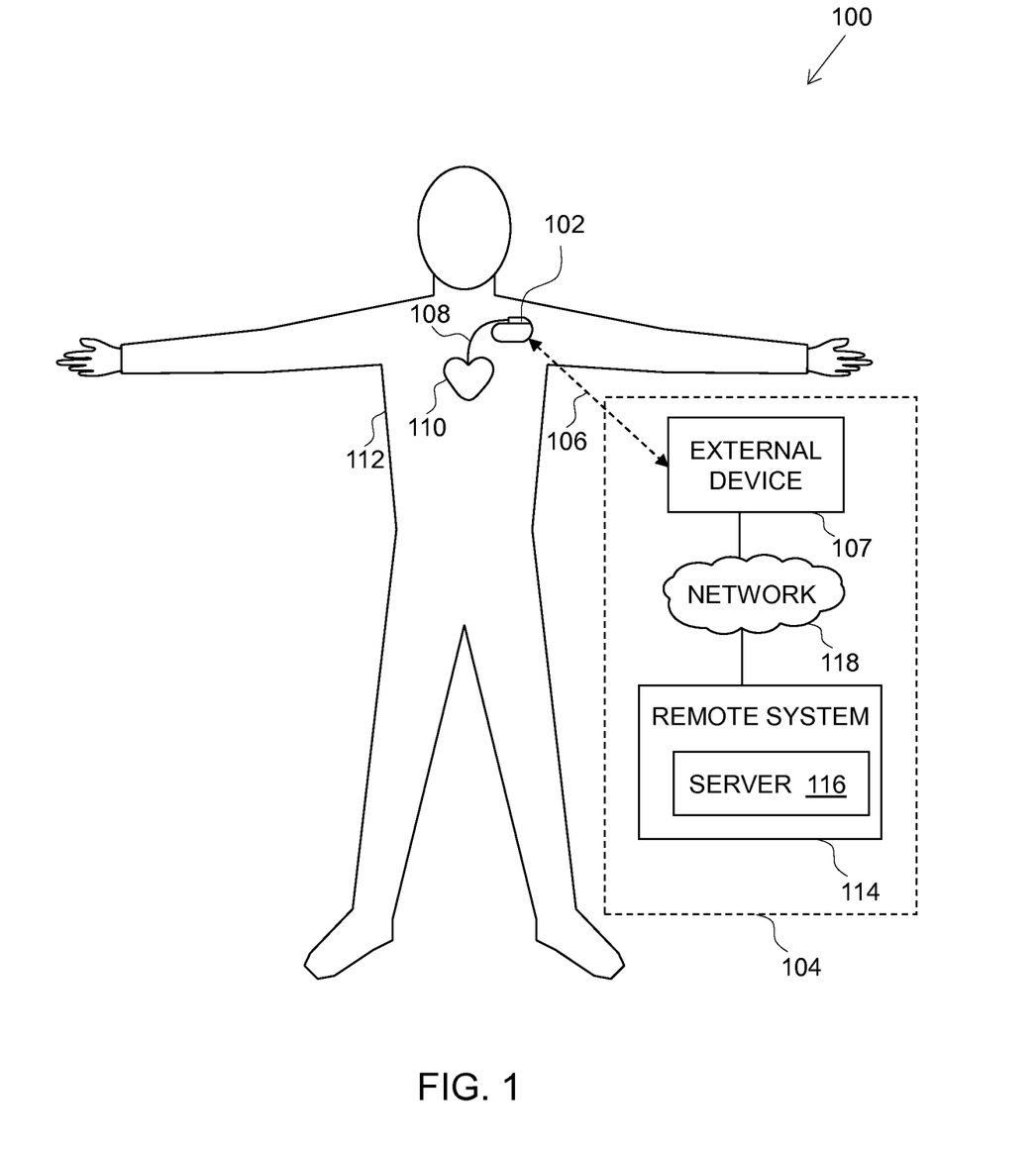
FIG. 1 is a schematic diagram illustrating portions of an example of a cardiac rhythm management (CRM) system.

FIG. 1 illustrates portions of an example of a CRM system 100 and portions of an environment in which the CRM system 100 can be used. The CRM system 100 can be configured to include an implantable medical device (IMD) 102 and an external system 104, and a communication link such as a telemetry link 106. The IMD 102 can include an electronic unit coupled by a cardiac lead 108, or additional leads, to a heart 110 of a subject 112. Examples of the IMD 102 can include, but are not limited to, pacemakers, pacemaker/defibrillators, cardiac resynchronization devices, cardiac remodeling control devices, and cardiac monitors. In an example, the IMD 102 can be configured to monitor health of the heart 110 and determine one or more abnormalities associated with the heart 110. The IMD 102 can take a necessary action, such as stimulating one or more portions of the heart 110 through the lead 108, to treat the one or more abnormalities.

In an example, the external system 104 can include an external device 107 configured to communicate bi-directionally with the IMD 102 such as through the telemetry link 106. For example, the external device 107 can include a programmer to program the IMD 102 to provide one or more therapies to the heart 110. In an example, the external device 107 can program the IMD 102 to detect presence of a conduction block in a right bundle branch (RBB) of the heart 110 and prevent dyssynchronous contraction of the heart 110 by providing a cardiac resynchronization therapy (CRT) to the heart 110.

In an example, the external device 107 can be configured to transmit data to the IMD 102 through the telemetry link 106. Examples of such transmitted data can include programming instructions for the IMD 102 to acquire physiological data, perform at least one self-diagnostic test (such as for a device operational status), or deliver at least one therapy or any other data. In an example, the IMD 102 can be configured to transmit data to the external device 107 through the telemetry link 106. This transmitted data can include real-time physiological data acquired by the IMD 102 or stored in the IMD 102, therapy history data, an operational status of the IMD 102 (e.g., battery status or lead impedance), and the like. The telemetry link 106 can include an inductive telemetry link or a far-field radio-frequency telemetry link.

In an example, the external device 107 can be a part of a patient management system that can include other devices such as a remote system 114 for remotely programming the IMD 102. In an example, the remote system 114 can be configured to include a server 116 that can communicate with the external device 107 through a telecommunication network 118 such as to access the IMD 102 to remotely monitor the health of the heart 110 or adjust parameters associated with the one or more therapies.

Figure 2:
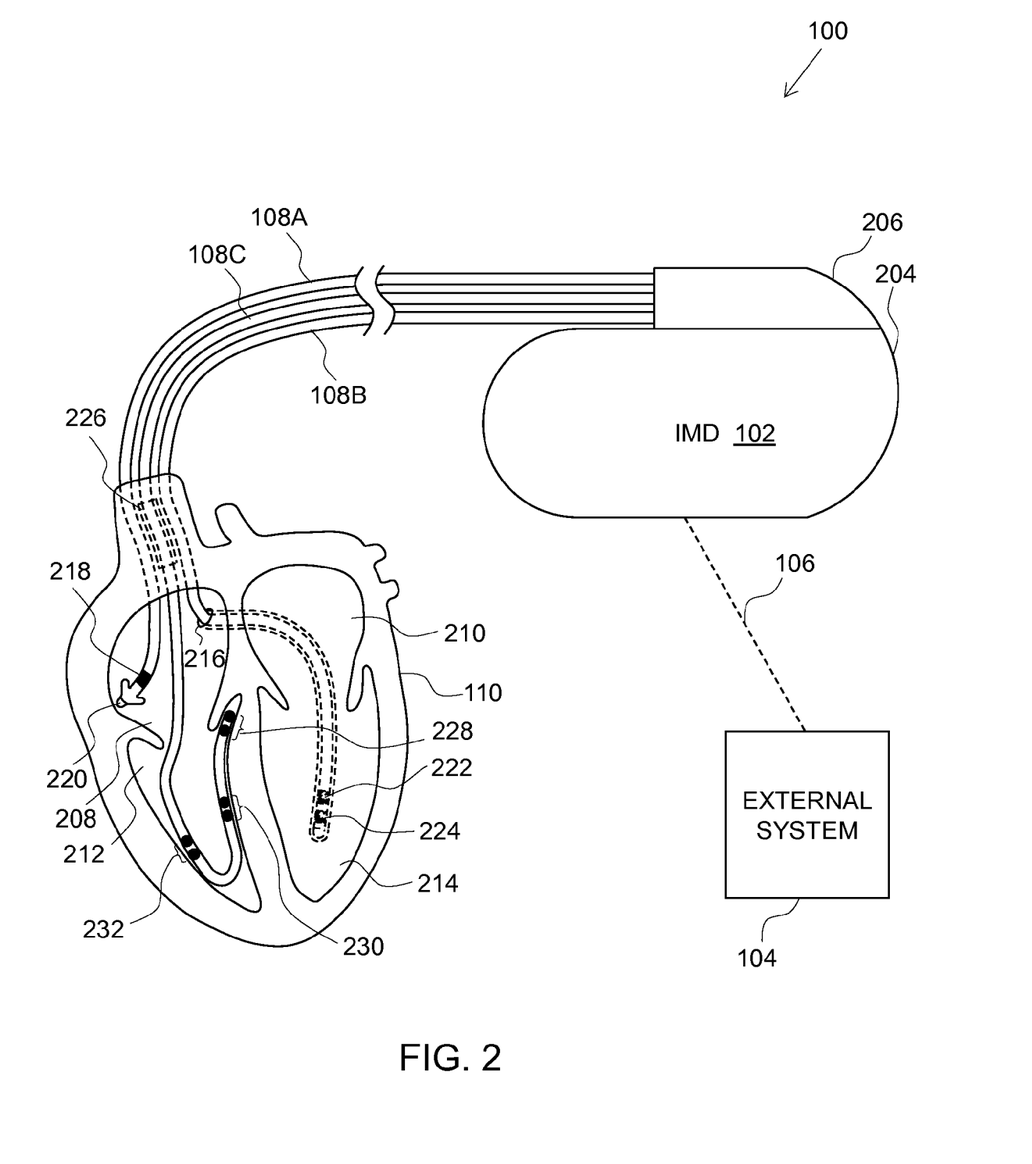
FIG. 2 is an illustration of portions of an example of the CRM system.

The present methods, systems, and devices can provide effective BiV CRT to a patient or subject experiencing RBBB. FIG. 2 illustrates portions of another example of a CRM system 100 and portions of the environment in which the CRM system 100 operates. The IMD 102 of the CRM system 100 can include a hermetically-sealed housing 204 and a header 206 that extends from the housing 204. The header 206 can include one or more receptacles such as for receiving proximal ends of one or more leads such as a lead 108A, a lead 108B and a lead 108C (collectively referred to herein as leads 108). Distal ends of the leads 108 can be coupled to electrodes such as for providing pacing energy, defibrillation energy, or both, in conjunction with the electrodes disposed on or around the heart 110. The electrodes can also be used for sensing electrical activity of the heart 110, including electrical activity related to contractions of the atria or ventricles.

As shown in FIG. 2, the heart 110 includes a right atrium (RA) 208, a left atrium (LA) 210, a right ventricle (RV) 212, a left ventricle (LV) 214, and a coronary sinus 216 extending from the RA 208. In an example, lead 108A can be an intravascular RA lead that can extend from a superior vena cava (SVC) into the RA 208 and can include electrodes such as a ring electrode 218 and a tip electrode 220 such as for sensing signals, or delivering pacing therapy, or both, to the RA 208. In an example, lead 108B can be an intravascular coronary sinus (CS)/left ventricle (LV) lead that can extend into the LV 214 through the CS 216. In an example, the LV lead 108B can include ring electrodes 222 and 224 through which intrinsic electrical heart signals can be sensed. In some examples, electro-stimulation energy can be delivered using the LV lead, but this stimulation may not be necessary where RBBB is being treated and the intrinsic LV conduction path is intact.

In an example, lead 108C can be an intravascular right ventricle (RV) lead that can extend from the SVC into the RA 208, and then into the RV 212. The lead 108C can be configured to include a defibrillation coil electrode 226 such as to provide high energy shock therapy to the subject. The RV lead 108C can include a plurality of electrode pairs such as an electrode pair 228, electrode pair 230, and electrode pair 232 for sensing signals, delivering pacing therapy, or both. The RV lead 108C can be configured to achieve resynchronization of the RV 212.

The present methods, devices and systems can work in a variety of electrode configurations and with a variety of electrodes. In an example, the different implantable electrode configurations can be defined by various combinations of sensing and stimulating pairs of electrodes. The electrodes may be used to deliver cardioversion, defibrillation, pacing, or resynchronization therapy, or combinations thereof to at least one chamber of the heart 110.

To provide therapy for conduction disease of the RV of a patient or subject, electrical stimulation pulses are provided to a stimulation location in the His bundle. The His bundle is typically located just below the tricuspid valve between the RA 208 and RV 212. The stimulation location is a point distal to the location of RV conduction block in the right branch of the His bundle. The right branch of the His bundle refers to that part of the HIS bundle that conducts impulses to the RV, and a portion of the right branch of the HIS bundle is accessible from the RV. If the electrical stimulation is not successful in circumventing the conduction block, electrical stimulation pulses can be provided to one or more portions of the RV 212 to address cardiac arrhythmias caused by RBBB. The IMD 102 can be configured to select at least one electrode pair from a plurality of electrode pairs of the RV lead 108C depending upon the location of the RV conduction block and deliver an electrical stimulation pulse through the selected electrode pair. A selective stimulation of the one or more portions of the RV 212 as part of CRT can synchronize contraction of the RV 212 and LV 214 and thereby improve the performance of the hemodynamic system of the subject 112.

Figure 3:
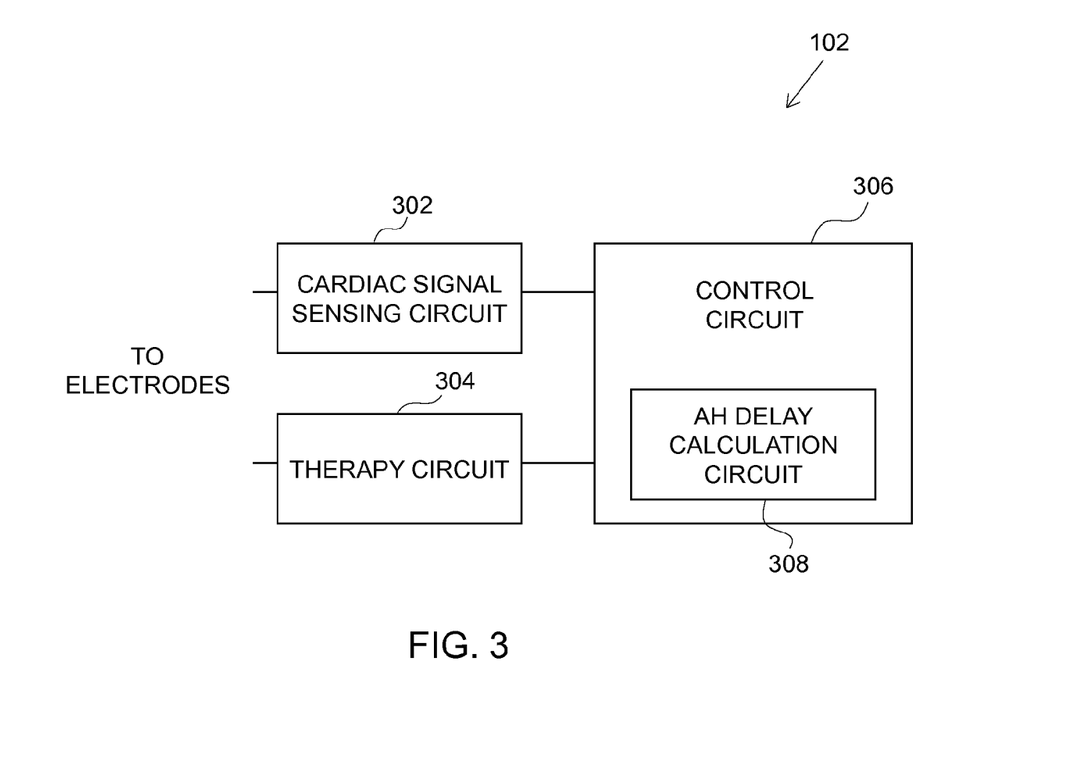
FIG. 3 is a block diagram illustrating portions of an example of an implantable medical device (IMD) of the CRM system of FIGS. 1 and 2.

FIG. 3 is a block diagram illustrating an example of the IMD 102. In an example, the IMD 102 can be configured to include a cardiac signal sensing circuit 302, a therapy circuit 304, and a control circuit 306. The control circuit 306 is communicatively coupled to the cardiac signal sensing circuit 302 and therapy circuit 304 to provide a therapy to resynchronize the ventricles de-synchronized due to presence of RBBB. The communicative coupling allows the control circuit 306 to communicate electrical signals with the cardiac signal sensing circuit 302 and the therapy circuit 304 even though there may be intervening circuitry between the control circuit 306, the cardiac signal sensing circuit 302, and the therapy circuit 304.

The cardiac signal sensing circuit 302 senses an intrinsic depolarization event in an atrium of the subject. In an example, the cardiac signal sensing circuit 302 can sense the atrium depolarization event using one or more signals as determined from the electrodes (e.g., the ring electrode 218 or the tip electrode 220 in FIG. 2). In an example, the one or more signals can be an impedance vector signal, pressure signal, contraction pattern, electrocardiogram (EGM) signal or any other signal. As described previously herein, the IMD 102 can be electrically coupled to electrodes such as the electrode pair 228, electrode pair 230, and electrode pair 232 that are implantable within the heart 110 through the RV lead 108C. The electrode pair 228 can be placed at a location in the right branch of the His bundle of the subject 112. The therapy circuit 304 can be electrically connected to a first electrode pair, such as electrode pair 228, to deliver an electrical stimulation pulse to the His bundle region of the heart 110. In an example, the electrode pair 228 can be disposed in the His bundle region in a manner such that the stimulation location is distal to a location of the conduction block in the right branch of the His bundle.

The control circuit 306 can include a processor (e.g., a microprocessor digital signal processor, application specific integrated circuit (ASIC) or other type of processor) interpreting or executing instructions in software modules or firmware modules. The control circuit 306 can include other circuits or sub-circuits to perform the function described. These circuits may include software, hardware, firmware, or any combination thereof. The control circuit 306 includes a AH delay calculation circuit 308 that can calculate an optimal value for a paced AH delay interval. The paced AH delay interval can be defined as a time interval from the sensed intrinsic atrial event to delivery of the electrical stimulation pulse to the stimulation location in the His bundle of the subject 112. The paced AH delay interval is shorter than an intrinsic AH delay interval. In an example, the intrinsic AH delay interval is a time interval from a sensed intrinsic atrial depolarization event to a corresponding intrinsic depolarization event of the His bundle. The intrinsic AH delay interval can be determined (e.g., by an action potential mapping procedure) and the paced AH delay specified (e.g., programmed) accordingly.

In an example, the control circuit 306 can be configured (e.g., by programming or logic circuits) to initiate delivery of the electrical stimulation pulse to the stimulation location in the His bundle according to the calculated paced AH delay interval and in response to the sensed intrinsic depolarization event sensed in the atrium of the subject 112. The His bundle stimulation can excite the rapid intrinsic conduction system of the heart 110 and shorten or minimize the slower cell to cell propagation of the stimulation. As a result, the His bundle stimulation can provide physiologic activation of the ventricles and thereby correct the RBBB while maintaining intrinsic activation of the LV 214.

Figure 4:
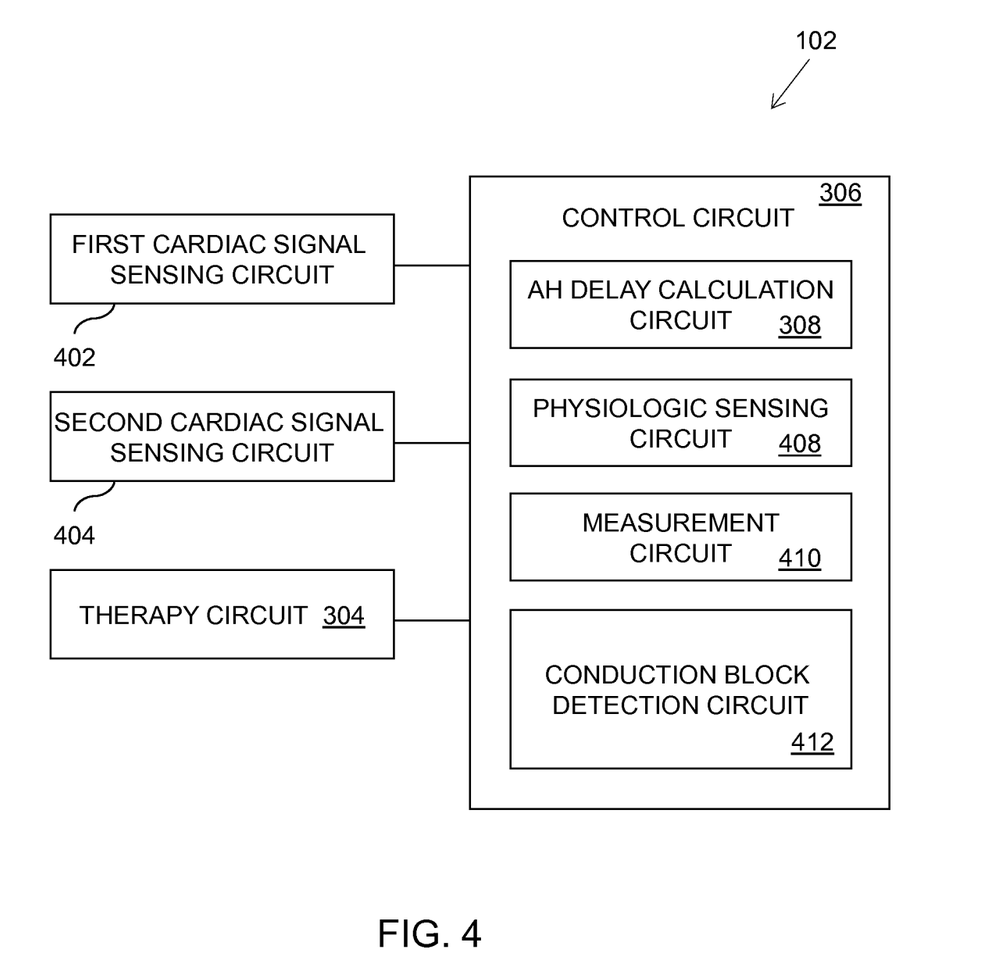
FIG. 4 is a block diagram illustrating portions of another example of an IMD.

FIG. 4 is a block diagram illustrating portions of an example of the IMD 102 of FIGS. 1-3. The IMD 102 can be configured to include a first cardiac signal sensing circuit 402, a second cardiac signal sensing circuit 404, the therapy circuit 304 and the control circuit 306. The control circuit 306 is communicatively coupled with the first cardiac signal sensing circuit 402, the second cardiac signal sensing circuit 404 and the therapy circuit 304, and initiates delivery of pacing pulses to at least one electrode of the plurality of electrode pairs such as to provide CRT.

The first cardiac signal sensing circuit 402, the second cardiac signal sensing circuit 404 and the therapy circuit 304 can be electrically connected to a plurality of electrodes. The plurality of electrodes can include a first electrode pair, such as the electrode pair 228 and a second electrode pair (e.g., electrode pair 230 or the electrode pair 232), and at least one electrode of the second electrode pair can be configured (e.g., by shape and size) for placement at a location distal from the stimulation location in the His bundle. In other words, the location of the at least one electrode of the second electrode pair is distal from the location of the first electrode pair. The second electrode pair can be configured to provide the electrical stimulation pulse to one or more portions of the RV 212 (e.g., a position approximately mid-septum in the RV, at an apical position of the septum in the RV, or a position on the RV free wall). In this way, if pacing stimuli delivered by the first electrode pair (e.g., located at the His bundle) is not effective in treating the RBBB, a different set of electrodes located farther along the conduction system (e.g., located mid-septum in the RV) can be used to correct the conduction block.

According to some examples, the paced AH delay used to deliver the pacing therapy can be calculated using the AH delay calculation circuit 308. In an example, the first cardiac signal sensing circuit 402 can be configured to sense an intrinsic depolarization event (RA) in an upper portion of the RA 208 of the subject 112 (e.g., using one or more electrodes placed high in the RA) and the second cardiac signal sensing circuit 404 can be configured to sense an intrinsic depolarization event (RA') in a lower portion of the RA 208. Using the sensed intrinsic depolarizations, the AH delay calculation circuit 308 can determine an intra-atrial delay (RA-RA') and can calculate the paced AH delay interval as a function of the RA-RA' time interval. In an example, the AH delay calculation circuit 308 calculates the paced AH delay interval (AHD) according to an equation: AHD=K1 *(RA-RA')+K2, wherein K1 and K2 are specified (e.g., programmed) constants. In an example, the constants can be specified to provide a linear relationship between the RA-RA' interval and the calculated paced AH delay interval. In another example, the constants K1 and K2 can be determined from a regression analysis of clinical population data.

In an example, the first cardiac signal sensing circuit 402 can include a bipolar electrode pair and the second cardiac signal sensing circuit 404 can include a unipolar electrode pair. In other words, the first cardiac signal sensing circuit 402 senses the intrinsic depolarization event (RA) in the upper portion of the RA 208 using the bipolar electrode pair and the second cardiac signal sensing circuit 404 senses the intrinsic depolarization event (RA') in the lower portion of the RA 208 using the unipolar electrode pair. In another example, the first cardiac signal sensing circuit 402 includes a first bipolar electrode pair for positioning at the upper RA and the second cardiac signal sensing circuit 404 includes a second bipolar electrode pair for positioning at the lower RA. The electrodes used to sense depolarizations in the RA may be included on a single lead implantable in the RA.

The AH delay calculation circuit 308 may use other time intervals to determine the paced AH delay. In an example, the first cardiac signal sensing circuit 402 can be configured to sense a first intrinsic depolarization event (RA) in the right atrium and the second cardiac signal sensing circuit 404 can be configured to sense a second intrinsic depolarization event (LA) in the left atrium. The AH delay calculation circuit 308 can determine an RA-LA time interval (an inter-atrial time interval) and can calculate the paced AH delay interval as a function of the RA-LA time interval. In an example, the AH delay calculation circuit 308 can be configured to calculate the paced AH delay interval (AHD) according to an equation: AHD=K1 *(RA-LA)+K2, wherein K1 and K2 are specified constants. As in the intra-atrial example, the K1 and K2 constants can be specified to provide a linear relationship between the RA-RA' interval and the calculated paced AH delay interval. In another example, the constants K1 and K2 can be determined from a regression analysis of clinical population data.

According to some examples, a CRM system can include other sensors. These sensors may provide physiological signals that can be used to control activation of the RV and optimize hemodynamic performance. In an example, the IMD 102 may include a physiologic sensing circuit 408 and a measurement circuit 410. The physiologic sensing circuit 408 senses a time varying physiologic signal that can include physiologic information regarding the subject 112. Examples of the physiologic signal can include one or more of a heart sound signal and an intracardiac impedance signal. Other examples of physiologic signals include a transthoracic impedance signal and a respiration signal that can be used to determine patient tidal volume and patient minute volume. The measurement circuit 410 calculates a measure of hemodynamic performance using the physiologic signal after delivery of one or more electrical stimulation pulses to the stimulation location in the His bundle. In an example, the control circuit 306 may modify the paced AH delay interval (AHD) according to a hemodynamic performance as calculated by the measurement circuit 410. For instance, if the physiologic sensing circuit 408 includes a heat sound sensor, the control circuit may adjust the AH delay interval to optimize one or both of the magnitude of the S1 heart sound and the timing of occurrence of the S1 heart sound. Such adjustment may ensure that there is no or minimal compromise in LV function when normalizing activation of the RV as part of BiV pacing therapy. This may result in optimization of performance of the hemodynamic system of the subject.

As explained previously herein, multiple electrodes may be arranged in the right branch of the His bundle and in the RV. If pacing the HIS bundle is not effective in treating the conduction block, BiV pacing therapy can be delivered to the RV at a stimulation location distal from the His bundle. In an example, the control circuit 306 can include a conduction block detection circuit 412 that detects that the conduction block persists in the right branch of the His bundle upon delivery of the electrical stimulation pulse to the stimulation location in the His bundle. The conduction block detection circuit 412 can determine time intervals associated with ventricular depolarization events. If the RBBB condition persists in the presence of His bundle stimulation, depolarization at the RV free-wall will be late compared to depolarization of the LV free-wall. If the CRM system includes a lead arrangement as shown in FIG. 2, a persistence of RBBB may be detected by comparing signals sensed on the LV free wall using electrodes 222, 224 to signals sensed on the RV free-wall using electrode pair 232. The conduction block detection circuit 412 may determine that RBBB persists when detecting that no change in timing occurs between depolarization of the LV free-wall and depolarization of the RV free-wall in the presence of His bundle stimulation. If the CRM system does not include dedicated LV sensing electrodes, intrinsic events in the LV may be sensed using a far field sensing approach, such as by sensing between an electrode in electrode pair 230 and an electrode formed on the can or header of the IMD 102. If the CRM system does not include dedicated LV sensing capability, the conduction block detection circuit 412 may detect that RBBB persists when detecting that a time interval from stimulation of the His bundle to depolarization of the RV free-wall is greater than a specified threshold time duration. In response to the detection of the conduction block in the RBB of the His bundle, the conduction block detection circuit 412 can be configured to change the stimulation location to a location distal from the stimulation location in the His bundle.

For instance, in the example shown in FIG. 2, the control circuit 306 can initiate delivery of an electrical stimulation pulse to the stimulation location in the His bundle a paced AH delay interval after a sensed atrial depolarization event. A determination is made regarding the presence of the conduction block in the RBB after stimulation of the His bundle. If the conduction block detection circuit 412 determines that the conduction block persists, the conduction block detection circuit 412 can be configured to change the stimulation location from the His bundle to a location within the mid-septum to the apical-septum of the RV (e.g., using electrode pair 230) or to a location on the RV free wall (e.g., using electrode pair 232). If the stimulation location is changed from the His bundle to a location in the RV on the ventricular septum and the conduction block still persists, the conduction block detection circuit 412 can be configured to change the stimulation location from the location within the mid-septum to the apical-septum of the RV 212 to the location on the RV free wall.

If the stimulation location chosen is outside the His bundle of the RV, the control circuit 306 may initiate LV triggered pacing instead of timing the stimulation from an intrinsic atrial event. For instance, the second cardiac signal sensing circuit 404 can be configured to sense an intrinsic depolarization event in the ventricle (e.g., LV) of the subject 112 and in response to the sensed LV event, the control circuit 306 can initiate delivery of an electrical stimulation pulse to a location within the mid-septum to apical-septum of the RV using the electrode pair 230. Similarly, if the stimulation location is a location on the RV free-wall, the control circuit 306 may initiate delivery of an electrical stimulation pulse to a location on the RV free wall using the electrode pair 232 in response to a sensed LV event.

The LV triggered pacing may include pacing the RV slightly before an intrinsic event is expected or anticipated in the LV. The control circuit 306 may initiate delivery of an electrical stimulation pulse using the stimulation location distal from the stimulation location in the His bundle, and the electrical stimulation pulse can be initiated prior to an expected intrinsic depolarization event in the LV. Because it typically takes about 100 milliseconds (ms) for an electrical stimulation pulse delivered to the RV to reach the LV, a pace delivered to the RV slightly before (e.g., <100 ms) the expected intrinsic LV depolarization event will not inhibit intrinsic LV activation. Using a paced atrial to RV delay (A-RV delay) that is shorter than an intrinsic atrial to LV delay (A-LV delay) may provide a better response to therapy for patients with concomitant LBBB associated with the RBBB.

To provide therapy in anticipation of events in the LV, the control circuit 306 may monitor the intrinsic A-LV delay using the second cardiac signal sensing circuit 404 and pace the RV according to the intrinsic A-LV delay. For instance, the control circuit 306 may calculate a central tendency value of the measured intrinsic A-LV delay (e.g., an average value or median value) over multiple cycles and pace the RV slightly before expiration the central tendency value. In certain examples, the control circuit 306 may monitor a time interval between intrinsic ventricular depolarization events (LV-LV) and pace the RV according to the intrinsic LV-LV interval. For instance, the control circuit may pace the RV slightly before expiration of a central tendency value of the LV-LV interval.

The control circuit 306 may change the stimulation location to a location within the mid-septum to the apical-septum of the RV or to a location on the RV free wall in response to the measure of the hemodynamic performance. As explained previously herein, the CRM system may include one or more physiologic sensors, and the measurement circuit 410 may calculate a measure of hemodynamic performance using a physiologic signal. The control circuit 306 may change the stimulation location according to the measure of hemodynamic performance. For example, the CRM system may include an intracardiac impedance sensing circuit. An intracardiac impedance signal can provide an indication of stroke volume for one or both ventricles. If pacing the His bundle does not result in an improvement in cardiac stroke volume, or results in a change in stroke volume that is less than a specified threshold change, the control circuit 306 may change the stimulation location distal from the His bundle. For instance, the stimulation location can be changed to the location within mid-septum to apical-septum of the RV or to a location on the RV free wall such as to improve the ventricular synchronization and improve hemodynamic performance.

Figure 5:
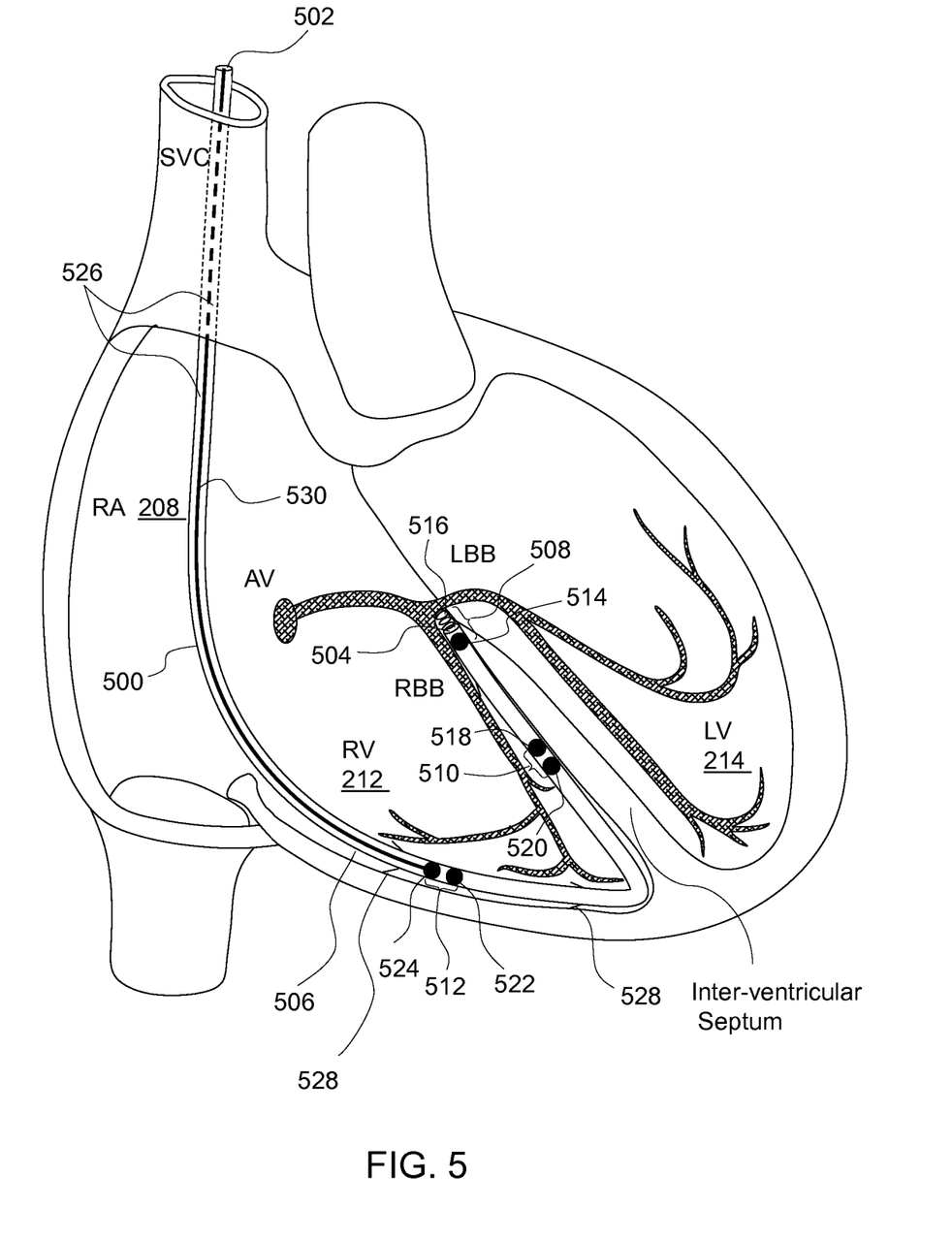
FIG. 5 is a schematic diagram illustrating an example of an implantable lead configured to be coupled to the IMD and positioned in a right ventricle of a subject.

FIG. 5 is a schematic diagram illustrating an example of an implantable lead 500 for correcting the conduction block in the RV 212 (e.g., RBBB) of the subject 112. The implantable lead 500 includes a lead body extending from a proximal end 502 to a distal end 504 and having an intermediate portion 506 therebetween. The lead body includes a plurality of conductors disposed therein to electrically connect electrodes of the lead to an IMD. The implantable lead 500 can include a first bipolar electrode pair 508 disposed at the distal end of the lead body and coupled to first and second conductors of the plurality of conductors, and a second bipolar electrode pair (e.g., 510) disposed at a position more proximal than the first bipolar pair and coupled to third and fourth conductors of the plurality of conductors. The lead body can include a shape bias configured to provide placement of the second bipolar pair at a location mid-septum to apical septum of the RV of a subject when the first electrode pair is placed at a location in a His bundle of the subject. The shape bias can be provided by insulation of the leads or can be provided by the plurality of conductors. Different lead sizes can be used to provide the proper placement of positioning of the second bipolar pair of electrodes. For instance, one lead size may include a separation of 3 centimeters (cm) between the first and second bipolar electrode pair, and a second lead size may include a separation of 4 cm or 6 cm between the first and second bipolar electrode pair.

In some examples, the implantable lead 500 can include a lumen to receive a guide wire. The guide wire can facilitate placement (e.g., by providing a stiffening force to the implantable lead) of the first bipolar electrode pair in the His bundle of the RV of the subject. When the guide wire is removed, the shape bias of the lead may result in placement of the second electrode pair 510 at the location mid-septum to apical septum of the RV.

The first bipolar electrode pair 508 can include a first electrode 514 and a second electrode 516 (e.g., a tip electrode). In an example, the implantable lead 500 can include a fixation device or mechanism at a tip of the implantable lead 500 such as to fixate the implantable lead to body tissues. The fixation device can be such as a helix or corkscrew which secures the implantable lead 500 to the tissues. In an example, one of the electrodes such as the second electrode 516 can be incorporated in the fixation device itself. Though, the FIG. 5 shows the implantable lead 500 using an active fixation mechanism/device, but other ways of fixation may also be adopted. In an example, the second bipolar electrode pair 510 is disposed at a position more proximal than the first bipolar electrode pair 508 and the second bipolar electrode pair 510 can include a third electrode 518 and a fourth electrode 520.

In an example, the implantable lead can include a third bipolar electrode pair 512 disposed at a position more proximal than the second bipolar electrode pair 510, and the third bipolar electrode pair 512 can include a fifth electrode 522 and a sixth electrode 524. The lead body can include a shape bias that provides placement of the third bipolar electrode pair 512 at a location on the free wall of the RV 212 when the first bipolar electrode pair 508 is placed at a location in the His bundle of the subject 112. As illustrated in the FIG. 5, the implantable lead 500 can be configured to include fixation mechanisms such as one or more tines 528 at one or more locations along the implantable lead to provide support to the implantable lead 500 in one or more portions of the RV 212.

The electrodes of the first bipolar electrode pair 508 can be coupled to a respective first conductor and second conductor. The electrodes of the second bipolar electrode pair 510 can be coupled to a respective third conductor and fourth conductor. The electrodes of the third bipolar electrode pair 512 can be coupled to a respective fifth conductor and sixth conductor. As illustrated in the FIG. 5, the implantable lead 500 includes a conductor 530 such to electrically connect the sixth electrode 524 of the third bipolar electrode pair 512 to the pulse generator of the IMD 102. Similarly, remaining electrode pairs are coupled to the respective conductors (not shown for simplicity of the drawing) of the plurality of conductors of the implantable lead 500.

In an example, each bipolar electrode pair of the implantable lead 500 can be configured to couple to an international standard one (IS1) type connector of the pulse generator of the IMD 102 through the respective conductors. For example, the first bipolar electrode pair 508 is coupled to the IS1-type connector through the first conductor and the second conductor. In an example, six conductors of the aforementioned three bipolar electrode pairs are coupled to three IS1-type connectors of the pulse generator. In some examples, the IMD includes a fourth IS1-type connector for connection to a LV lead.

In an example, the IMD 102 can be configured to deliver the electrical stimulation pulse to the His bundle using the first bipolar electrode pair 508 such as to correct the conduction disease in the RV 212 of the subject 112. The IMD 102 can be configured to deliver the electrical stimulation pulse to the mid-septum to the apical septum of the RV 212 using the second bipolar electrode pair 510 or to the RV free wall using the third bipolar electrode pair 512 on determining that the His bundle stimulation is not able to correct or otherwise treat the conduction disease in the RV 212. Other arrangements may include an implantable lead including the first bipolar electrode pair 508 and electrode pair 512 as the second electrode pair.

Figure 6:
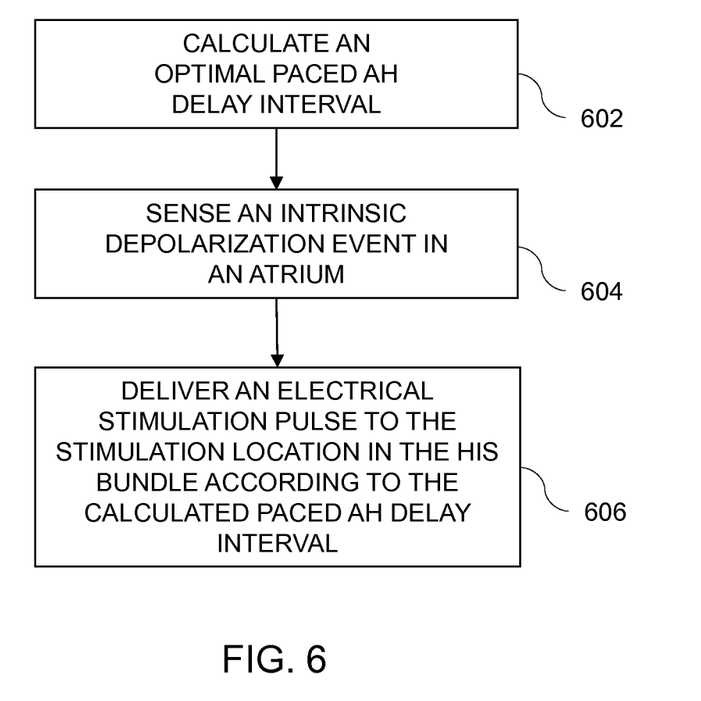
FIG. 6 is a flow diagram of an exemplary method for operating an IMD to correct a conduction disease in the right ventricle of the subject.

FIG. 6 is a flow diagram of an exemplary method 600 for operating the IMD 102 to correct conduction disease in the right ventricle (RV) of the subject 112. At 602, the method can include calculating an optimal paced AH delay interval. In an example, the optimal paced AH delay interval is the time interval from a sensed intrinsic atrial event to delivery of an electrical stimulation pulse to a stimulation location in the His bundle of the subject 112. The stimulation location is distal from the location of the conduction block (e.g., distal from a lesion). In an example, the paced AH delay interval can be calculated as a function of an intra-atrial time interval that can include a time interval between an atrial depolarization event sensed in an upper region of the RA 208 to an atrial depolarization event sensed in a lower region of the RA (RA'). In such an example, the paced AH delay interval (AHD) can be calculated using a formula AHD=K1 *(RA-RA')+K2, wherein K1 and K2 are specified constants and RA-RA' is the intra-atrial time interval.

In an example, the paced AH delay interval can be calculated as a function of an inter-atrial time interval that can include a time interval between an atrial depolarization event sensed in the RA 208 to an atrial depolarization event sensed in the LA 210. In such an example, the paced AH delay interval (AHD) can be calculated using a formula AHD=K1 *(RA-LA)+K2, wherein K1 and K2 are specified constants and (RA-LA) is the inter-atrial time interval.

At 604, the method can include sensing an intrinsic depolarization event in the atrium of the subject 112. At 606, the method can include delivering an electrical stimulation pulse to a stimulation location in the His bundle according to the calculated paced AH delay interval. In an example, the stimulation location is distal to a location of the RV conduction block in the right branch of the His bundle and the paced AH delay interval is shorter than the intrinsic AH delay interval.

The method 600 can include detecting that conduction block persists in the right branch of the His bundle upon delivery of the electrical stimulation pulse to the stimulation location. Upon detecting that conduction block persists in the right branch of the His bundle, the method 600 can include changing the stimulation location to a location that is distal from the stimulation location in the His bundle. In an example, the method 600 can change the stimulation location from the His bundle to a location within the mid-septum to the apical-septum of the RV 212. The delivery of a pacing pulse at this location can be triggered upon sensing a depolarization event sensed in the LV 214. In an example, the method 600 can include changing the stimulation location to a location on the RV free wall and triggering the pacing of this location upon sensing the depolarization event in the LV 214.

In an example, the method 600 can include obtaining a measure of hemodynamic performance after delivery of one or more electrical stimulation pulses to the stimulation location in the His bundle and changing the paced AH delay interval according to the measure of hemodynamic performance. In an example, the method 600 can measure the hemodynamic performance using one or more of a heart sound signal and an intracardiac impedance signal and/or any other physiological signal.

In an example, the method 600 can include obtaining a measure of hemodynamic performance after delivery of one or more electrical stimulation pulses to the stimulation location in the His bundle and changing, according to the measure of hemodynamic performance, the stimulation location to a location within the mid-septum to the apical-septum of the RV or to a location on the RV free wall.

In contrast to conventional BiV pacing, the methods, systems and devices described herein take advantage of the native or normal conduction path of the RV of the subject. By initiating RV depolarization using the His bundle, disadvantages of CRT for RBBB can be overcome to provide effective therapy for RV conduction block.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc., are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. The code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method comprising:
   calculating, by a medical device, an optimal paced atrial-His bundle (AH) delay interval, wherein a paced AH delay is a time interval from a sensed intrinsic atrial event to delivery of an electrical stimulation pulse to a stimulation location in a His bundle of the subject, wherein the stimulation location is distal to a location of RV conduction block in a right branch of the His bundle;
   sensing an intrinsic depolarization event in an atrium of the subject; and
   delivering an electrical stimulation pulse to the stimulation location in the His bundle according to the calculated paced AH delay interval, wherein the paced AH delay interval is shorter than an intrinsic AH delay interval, wherein an intrinsic AH delay interval is a time interval from the sensed intrinsic atrial depolarization event to a corresponding intrinsic depolarization event of the His bundle.

2. The method of claim 1, wherein calculating the paced AH delay interval includes:
   determining, by the medical device, an intra-atrial time interval, wherein the intra-atrial time interval includes a time interval between an atrial depolarization event sensed in an upper region of a right atrium (RA) to an atrial depolarization event sensed in a lower region of the right atrium (RA'); and
   calculating the paced AH delay interval as a function of the intra-atrial (RA-RA') time interval.

3. The method of claim 1, wherein calculating the paced AH delay interval includes:
   determining, by the medical device, an inter-atrial time interval, wherein the inter-atrial time interval includes a time interval between an atrial depolarization event sensed in a right atrium (RA) to an atrial depolarization event sensed in a left atrium (LA); and
   calculating the paced AH delay interval as a function of the inter-atrial (RA-LA) time interval.

4. The method of claim 1, including:
   detecting, by the medical device, that conduction block persists in the right branch of the His bundle upon delivery of the electrical stimulation pulse to the stimulation location; and
   changing, by the medical device in response to the detecting, the stimulation location to a location distal from the stimulation location in the His bundle.

5. An apparatus comprising:
   a first cardiac signal sensing circuit configured to sense an nnrinsic depolarization event in an atrium of a subject;
   a first implantable electrode pair, wherein at least one electrode of the first implantable electrode pair is configured for placement at a location in a right branch of a His bundle of the subject;
   a therapy circuit electrically connectable to the first implantable electrode pair; and
   a control circuit communicatively coupled to the first cardiac signal sensing circuit and the therapy circuit, wherein the control circuit includes an AH delay calculation circuit configured to calculate an optimal paced AH delay interval, wherein a paced AH delay interval is shorter than an intrinsic AH delay interval;
   wherein the control circuit is configured to initiate delivery of an electrical stimulation pulse to a stimulation location that is distal to a location of RV conduction block in a right branch of the His bundle, and wherein the delivery of the electrical stimulation pulse is initiated in response to an intrinsic depolarization event sensed in the atrium and after the calculated paced AH delay interval.

6. The apparatus of claim 5, including:
   a second cardiac signal sensing circuit, wherein the first cardiac signal sensing circuit is configured to sense a first intrinsic depolarization event (RA) in an upper portion of a right atrium of the subject, and the second cardiac signal sensing circuit is configured to sense a second intrinsic depolarization event (RA') in a lower portion of the right atrium;
   wherein the AH delay calculation circuit is configured to determine an RA-RA' time interval and calculate the paced AH delay interval as a function of the RA-RA' time interval.

7. The apparatus of claim 6, wherein the AH delay calculation circuit is configured to calculate the paced AH delay interval (AHD)) according to AHD=K1*(RA-RA')+K2, wherein K1 and K2 are specified constants.

8. The apparatus of claim 6, wherein the first cardiac signal sensing circuit includes a bipolar electrode pair and the second cardiac signal sensing circuit includes a unipolar electrode pair.

9. The apparatus of claim 5, including:
   a second cardiac signal sensing circuit, wherein the first cardiac signal sensing circuit is configured to sense a first intrinsic depolarization event (RA) in the right atrium, and the second cardiac signal sensing circuit is configured to sense a second intrinsic depolarization event (LA) in the left atrium;

wherein the AH delay calculation circuit is configured to determine an RA-RA' time interval and calculate the paced AH delay interval as a function of the RA-LA time interval.

10. The apparatus of claim 9, wherein the AH delay calculation circuit is configured to calculate the paced AH delay interval (AHD) according to AHD=K1 *(RA-LA)+K2, wherein K1 and K2 are specified constants.

11. The apparatus of claim 5, including:
a second implantable electrode pair, wherein at least one electrode of the second implantable electrode pair is configured for placement at a location distal from the stimulation location in the His bundle: and
a second cardiac signal sensing circuit configured to sense an intrinsic depolarization event in a ventricle of the subject,
wherein the control circuit includes a conduction block detection circuit configured to:
detect conduction block in the right branch of the His bundle upon delivery of the electrical stimulation pulse to the stimulation location in the His bundle; and
change, in response to detecting that conduction block persists in the right branch of the His bundle, the stimulation location to the location distal from the stimulation location in the His bundle.

12. The apparatus of claim 11,
wherein the second implantable electrode pair includes at least one electrode configured for placement at a location within mid-septum to apical-septum of a right ventricle (RV), and
wherein the control circuit is configured to initiate delivery of an electrical stimulation pulse, using the second implantable electrode pair, that is triggered by a depolarization event sensed in a left ventricle (LV).

13. The apparatus of claim 11, wherein the control circuit is configured to initiate delivery of an electrical stimulation pulse using the stimulation location distal from the stimulation location in the His bundle, wherein the electrical stimulation pulse is initiated prior to an expected intrinsic depolarization event in the LV.

14. The apparatus of claim 5, including:
a second implantable electrode pair, wherein at least one electrode of the second implantable electrode pair is configured for placement at a location on the RV free wall; and
a second cardiac signal sensing circuit configured to sense an intrinsic depolarization event in a ventricle of the subject,
wherein the control circuit includes a conduction block detection circuit configured to:
detect conduction block in the right branch of the His bundle upon delivery of the electrical stimulation pulse to the stimulation location in the His bundle;
change the stimulation location to a location on the RV free wall; and
trigger the electrical stimulation pulse according to a depolarization event sensed in a left ventricle (LV).

15. The apparatus of claim. 5, including:
a physiologic sensing circuit configured to sense a time varying physiologic signal, wherein the physiologic signal includes physiologic information of the subject,
wherein the control circuit includes a measurement circuit configured to calculate a measure of hemodynamic performance using the physiologic signal after delivery of one or more electrical stimulation pulses to the stimulation location in the His bundle, and
wherein the control circuit is configured to change the paced AH delay interval according to the measure of hemodynamic performance.

16. The apparatus of claim. 15, wherein the physiologic signal includes one or more of a heart sound signal and an intracardiac impedance signal.

17. The apparatus of claim 15, wherein the control circuit is configured to change, according to the measure of hemodynamic performance, the stimulation location to a location. within mid-septum to apical-septum of the RV or to a location on the RV free wall.

18. An implantable lead including:
a lead body extending from a proximal end to a distal end having an intermediate portion therebetween, wherein the lead body includes a plurality of conductors disposed therein;
a first bipolar electrode pair disposed at the distal end of the lead body and coupled to first and second conductors attic plurality of conductors;
a second bipolar electrode pair disposed at a position more proximal than the first bipolar pair and coupled to third and fourth conductors of the plurality of conductors; and
wherein the lead body includes a shape bias configured to provide placement of the second bipolar pair at a location mid-septum to apical septum of the right ventricle of a subject when the first electrode pair is placed at a location in a His bundle of the subject.

19. The implantable lead of claim 18, including:
a third bipolar electrode pair disposed at a position more proximal than the second bipolar pair and coupled to fifth and sixth conductors of the plurality of conductors,
wherein the lead body shape includes a shape bias configured to provide placement of the third bipolar electrode pair at a location on a free wall of the RV when the first electrode pair is placed at a location in a His bundle of the subject.

20. The implantable lead of claim 18, including a lumen configured to receive a guide wire configured to facilitate placement of the first bipolar electrode pair in the His bundle.

* * * * *